United States Patent [19]

Sokol et al.

[11] 4,182,612

[45] Jan. 8, 1980

[54] METHOD FOR DYEING HUMAN HAIR WITH CATIONIC POLYMERIC DYES

[75] Inventors: Phillip E. Sokol, Rockville, Md.; Hu-Chu Tsai, Hingham, Mass.

[73] Assignee: The Gillette Company, Boston, Mass.

[21] Appl. No.: 763,850

[22] Filed: Jan. 31, 1977

[51] Int. Cl.$^2$ .............................................. A61K 7/13
[52] U.S. Cl. ..................................... 8/10.1; 8/DIG. 7; 8/10; 260/367; 260/368; 525/328; 525/330; 525/336; 525/359; 525/374; 525/376; 525/375; 525/383
[58] Field of Search ....................... 8/10, DIG. 7, 10.1; 260/144, 367, 368, 78 SC; 526/15, 17, 23, 46, 49, 50, 51, 53

[56] References Cited

U.S. PATENT DOCUMENTS

| | | | |
|---|---|---|---|
| 3,251,743 | 5/1966 | Hahn et al. | 8/10.1 |
| 3,567,678 | 3/1971 | Kalopissis | 8/10.1 X |
| 3,617,165 | 11/1971 | Kalopissis | 8/10.1 |
| 3,619,101 | 11/1971 | Kalopissis | 8/10.1 |
| 3,763,086 | 10/1973 | Kalopissis et al. | 8/10.1 X |
| 3,790,512 | 2/1974 | Wagner et al. | 8/10.1 X |
| 3,797,994 | 3/1974 | Kalopissis | 8/10.1 |
| 3,912,808 | 10/1975 | Sokol | 8/10.1 X |
| 3,920,855 | 11/1975 | Dawson et al. | 260/144 X |

OTHER PUBLICATIONS

Chemical Abstracts, 60:P5673h, (1964).

*Primary Examiner*—Bernard Helfin
*Assistant Examiner*—Vera C. Clarke
*Attorney, Agent, or Firm*—Richard A. Wise; Leonard J. Janowski

[57] ABSTRACT

A new class of water soluble cationic dyes especially useful in the rapid dyeing of hair prepared by the covalent reaction of visibly colored optical chromophores with selected polymeric backbones containing at least one primary, secondary, or tertiary amino group per repeating unit.

7 Claims, No Drawings

METHOD FOR DYEING HUMAN HAIR WITH CATIONIC POLYMERIC DYES

The desire to change the natural color of human hair has led, since early recorded history, to the application of various types of natural and man-made materials in attempts to alter it. The historical development of hair coloring has followed the traditional use of plant derivatives such as henna, camomile, and wood extracts through the use of metallic compounds usually promoted as "color restorers" to the modern development of synthetic organic compounds suitable for dyeing hair and other animal fibers. Modern hair coloring compositions are usually described as either temporary colorings, semi-permanent dyes, or permanent (or oxidation) dyes.

Temporary coloring products for hair are of comparatively recent origin and usually take the form of rinse-type products comprising an aqueous solution of tartaric or other suitable acid with a water soluble dye. While many types of dyes are theoretically suitable for such products, most manufacturers choose dyes from among those listed as suitable for cosmetics by the United States Food and Drug Administration. Although products of this type are fast to simple rinsing with water, they are intended to be removable with the next normal shampooing of the hair.

At the other extreme are the permanent or oxidation dyes which have been increasingly exploited since the middle of the nineteenth century. Modern oxidation dye compositions consist of complex mixtures of aromatic amino and related compounds known as color-forming intermediates mixed with color modifiers such as metadiamines and various polyphenols. These mixtures are typically applied to the hair along with aqueous hydrogen peroxide, the peroxide serving to not only develop the intermediates by oxidation but also to lighten the natural color of the hair. As their name suggests, dyes of this type cannot be readily removed from the hair by shampooing or other simple means to restore its original color, leading to color differences between old and new growth where the hair has been dyed a color significantly different than the natural color.

Semi-permanent dyes, so named because they remain on the hair through several shampooings, gradually fading back to the natural hair color, are usually direct dyes usually applied without any bleaching action. Various direct dyes such as azo, nitro, and derivatives of naphthalene and anthraquinone are employed in the formulation of such products. Such effort has also been made to adapt textile industry reactive dye experience to the dyeing of hair. In general, however, reactive dye systems have proved more useful in the dyeing of other animal fibers such as wool or silk.

A comparatively recent development in the dyeing art involves the use of polymeric dyes formed by the reaction of colorless polymeric backbones bearing reactive sites with reactive chromophores to yield dyes having the general properties of the basic polymer but serving to impart color to the substrates to which they are applied. When produced for the treatment of hair, these colored polymers have generally been derivatives of polymers of the type suitable for hair setting use, typically applied from an aerosol package system. Such dyes are generally intended to be used for purposes of temporary coloring and, like the basic polymeric backbones, are designed to be shampoo removable. Examples of patents describing polymeric dyes of this type are U.S. Pat. No. 3,535,255 and U.S. Pat. No. 3,920,855.

One class of polymer which has found application in the hair treating art is the class of water soluble cationic polymers. Polymers of this type have been employed as hair conditioners in a variety of hair treating compositions. By virtue of the presence of cationic sites on the polymer backbones, primarily primary and secondary amino groups, such polymers have an affinity for hair keratin and are capable of being formulated in a manner to permit them to surround individual fibers with a conditioning coating which is resistant to the usual shampoo removal.

U.S. Pat. No. 3,920,855 describes dye compositions comprising chromophore groups which have been attached, by way of a sulfonamide linkage, to non-degradable polymeric backbones of a wide variety including cationic polyethylenimine polymers. The purpose of the dyes described in the patent is as food colors having sufficiently great molecular weight to prevent absorption from the gastrointestinal tract. The dyes described in this patent are prepared by the reaction of a polymer containing pendant amino groups such as polyethylenimine with a benzenesulfonyl chloride on which there is an acetylamino group. The subsequently formed sulfonamide-containing polymer is then treated with alkali to hydrolize off the acetyl group. This is then followed by reaction with nitrous acid to convert the pendant aromatic amino group to a diazonium salt which is then coupled with an appropriate coupler to form the polymeric dye.

The overall synthesis, however, is one in which primary and secondary amino groups attached to aliphatic carbon atoms undergo reaction and are converted to non-cationic functionalities. The resulting polymer is accordingly largely devoid of cationic character and has little affinity for any keratin substrate to which it might be applied.

It has now been found that a new class of water soluble dyes especially useful in the rapid dyeing of hair, but also useful in the dyeing of other substrates can be prepared by the covalent reaction of visibly colored optical chromophores with selected polymeric backbones containing at least one primary, secondary, or tertiary amino group per repeating unit. The resulting products are cationic polymeric dyestuffs capable of dyeing hair or other substrates rapidly in a wide variety of colors, leaving a desirable, smooth, coated feel upon the substrate. These dyes are generally resistant to removal by washing or shampooing, but can be lightened by conventional stripping methods as described herein. When used as hair dyes, the compositions of this invention, since they are water soluble, produce minimal skin staining when flushed from the skin with water. A further advantage in use as hair dyes resides in the lack of color build-up upon repeated use.

The polymeric backbones which may be used in preparing the dyes of this invention comprise (1) polyethylenimine having a molecular weight range of 300 to 200,000, (2) polydiallylamine having a molecular weight range of 10,000 to 2,000,000, and (3) the reaction products obtained by the condensation of alkylene polyamines having 3 or more primary, secondary, or tertiary amino groups separated by alkylene groups having 2 to 5 carbon atoms and having a molecular weight of 60 to 400 with difunctional compounds selected from the class consisting of dibasic acids having 2 to 54 carbon atoms, alpha-omega aliphatic dihalides having 2 to 10 carbon atoms, epihalohydrins and diepoxides having 4 to 18 carbon atoms, said reaction products having a molecular weight range of 1,000 to 100,000. These backbones may have up to 75% of their available primary or secondary amino groups reacted with alkylating or acylating agents having alkyl groups of 1 to 18 carbon atoms or with ethylene oxide.

In forming the dyes of this invention, the cationic polymeric backbones described above are covalently reacted with suitably substituted dyes or dye mixtures, as will be discussed below, taken from the class consisting of azo, anthraquinone, nitro, nitroso, stilbene, diphenylmethane, triarylmethane, xanthene, acridene, quinoline, methine, thiazole, indamine, indophenol, azine, thiazine, lactone, aminoketone, hydroxyketone, indigoid and phthalocyanine.

Useful dyeing results can be obtained with as little as 1% substitution of available amino groups or as much as 25%, but we have found that 2 to 10% substitution is preferred in that it produces good color intensity without too great a reduction of the cationic character of the polymeric backbone.

The condensation of dye chromophores with the polymeric backbones can be carried out via two different routes. The first of these is direct condensation in which the dye chromophore has a functional group capable of reacting with amino groups of the polymer to form a stable covalent bond. For example, polyethylenimine can be condensed with reactive anthraquinone and nitrobenzene chromophores such as 1-chloroanthraquinone; 2,5-dihydroxyanthraquinone or 2,4-dinitrochlorobenzene.

Dye chromophores which do not contain functional groups capable of reacting with the amino groups of the backbone polymers must first have a reactive group introduced by reaction with a suitable linking compound from the group shown below to yield, in each case, the indicated derivative.

TABLE I

| Linking Compound | Derivative Produced |
|---|---|
| vinyl sulfone | Dye-SO$_2$—CH=CH$_2$ |
| acylating agent | Dye—C(=O)—R<br>Where R=halogen, OH, OR$_1$, NH$_2$, NHR$_1$, N(R$_1$)$_2$, where R$_1$=C$_1$—C$_4$ alkyl or an organic anhydride residue. |
| cyanuric halide | Dye—C(=N—C(=N)—X)(—N=C(R)—N)<br>Where X=halogen<br>R=halogen or OR$_1$<br>Where R$_1$ = C$_1$ to C$_4$ alkyl |
| sulfonylating agent | Dye—SO$_2$—R<br>Where R=halogen, OH, OR$_1$, NH$_2$, NHR$_1$, N(R$_1$)$_2$, where R$_1$ = C$_1$—C$_4$ alkyl or an organic anhydride residue. |
| phosphorylating agent | Dye—P(=O)(R)—R<br>Where R=halogen, OH, OR$_1$, NH$_2$, NHR$_1$, N(R$_1$)$_2$, where R$_1$ = C$_1$—C$_4$ alkyl or an organic |

TABLE I-continued

| Linking Compound | Derivative Produced |
|---|---|
| | anhydride residue. |

EXAMPLE I

Preparation of a Yellow Polyethylenimine Dye 21.5 grams of polyethylenimine (m.w. 1200) was dissolved in 150 ml. of ethanol in a 300 ml. 3-neck flask equipped with a mechanical stirrer. 10.1 grams of 2,4-dinitrochlorobenzene was added over five minutes to the polyethylenimine solution and the mixture heated under reflux for one hour. The reaction was checked by thin layer chromatography using silica gel and chloroform solvent to make certain that all of the dye had reacted with the polymer. Ethanol was removed under vacuum and the residue dissolved in water to make a 20% yellow dye solution having a pH of 9.1.

EXAMPLE II

Red Polyethylenimine Dye 21.5 grams of polyethylenimine (m.w. 1200) was dissolved in 150 ml. of ethanol in a 200 ml. 3-neck flask equipped with a mechanical stirrer. 6.4 grams of 1-amino-5-chloroanthraquinone was added and the mixture heated under reflux for approximately 52 hours until thin layer chromatography indicated that all of the dye and polymer had reacted. Ethanol was then removed under vacuum. The resulting red dye was dissolved in water and neutralized to a pH of 7.0 with concentrated hydrochloric acid.

EXAMPLE III

Blue Polyethylenimine Dye

A 300 ml. 3-neck flask equipped with the mechanical stirrer was charged with 18.0 grams quinizarin, 6.0 grams leucoquinizarin, 15.8 grams boric acid, 16.8 grams p-toluidine hydrochloride, 4.7 grams sodium hydroxide and 100 ml. of ethanol. The mixture was heated under reflux for 6 hours, cooled and filtered. The resulting precipitate of 1-hydroxy-4-(p-toluidino)anthraquinone was triturated with aqueous 0.7% sodium hydroxide solution and recovered by filtration. The residue was washed free of alkali with water and dried in a vacuum oven.

6.6 grams of the 1-hydroxy-4-(p-toluidino)anthraquinone prepared above was added to a mechanical stirrer-equipped 3-neck flask containing 17.2 grams of polyethylenimine (m.w. 1200) in 50 ml. of ethanol. The mixture was heated under reflux for five hours after which ethanol was removed under vacuum. The resulting blue dye was dissolved in water and adjusted with concentrated hydrochloric acid to a pH of 6.0

EXAMPLE IV

Red Polyethylenimine Dye 3.7 grams of cyanuric chloride was dissolved in 45 ml. acetone and cooled to 0° C. in an ice bath. A slurry of 5.3 grams of 1-(2-aminoethyl)aminoanthraquinone, 1.7 grams sodium bicarbonate and 100 ml. of acetone was added to the solution. After maintaining the temperature at under 5° C. for one hour, the composition was stirred at room temperature for two days. The mixture was filtered and an orange colored precipitate of 2,4- dichloro-6[1-(2-aminoethyl)aminoanthraquinonyl]triazine was collected.

4.0 grams of polyethylenimine (m.w. 1200) was dissolved in 50 ml. of chloroform to which two grams of the condensation product obtained above was added. The mixture was heated under reflux for 2.5 hours after which the chloroform was removed under vacuum and the residue dissolved in water to make a 20% red dye solution.

EXAMPLE V

Red Polydiallylamine Dye 291.0 grams of diallylamine was neutralized with 250 ml. of concentrated hydrochloric acid and placed in a round bottom flask. 210 ml. of water and 12 ml. of t-butylhydroperoxide were added. The flask was then purged with nitrogen, stoppered, and placed in an oven at 65° C. for five days. The mixture was then stripped dry under vacuum and dissolved in 200 ml. of water to yield a dark brown polymer solution which was poured slowly into two liters of rapidly stirred ethanol. The resulting precipitate of polydiallylamine was collected and dried in an oven.

6.0 grams of polydiallylamine (derived from the polydiallylamine hydrochloride obtained above by alkalizing with 10% sodium hydroxide followed by extraction with chloroform and stripping) was dissolved in 50 ml. of chloroform. 3.0 grams of Procinyl Red, a chlorotriazinyl reactive dye, was added to the mixture and heated under reflux for 2.5 hours until thin layer chromatography indicated reaction was complete. Chloroform was removed under vacuum and the resulting red dye dissolved in water to make a 10% solution.

EXAMPLE VI

Yellow Ethoxylated Polyethylenimine Dye 10.0 grams of polyethylenimine (m.w. 600) was dissolved in 100 ml. of chloroform containing 5.0 grams of Procinyl Yellow, a chlorotriazinyl reactive dye, and the mixture heated under a vacuum and the residue dissolved in 75 ml. of water. A dry ice condenser was connected to the reaction flask and the colored polymer solution heated to reflux. Ethylene oxide gas was bubbled into the solution until ten grams had been absorbed. The resulting ethoxylated polyethylenimine polymer had a weight ratio of polyethylenimine/dye/ethylene oxide of 2:1:2.

EXAMPLE VII

Red Acylated Polyethylenimine Dye 7.2 grams methyl formate was added drop-wise to 12.9 grams of polyethylenimine (m.w. 1200) at room temperature in a 3-neck flask equipped with a mechanical stirrer, the mixture being stirred for two hours after completion of the addition. The methanol formed in the reaction was then removed under vacuum. After the addition of 6.5 grams of Procinyl Red and 10 ml. of chloroform, the mixture was maintained at 85° C. for 0.5 hour. The chloroform was removed under vacuum and the resulting red dye dissolved in water to make a 15% solution.

Using the general preparative procedures described above, the following cationic polymers and dye intermediates can be reacted to produce cationic polymeric dyes having the colors indicated.

TABLE II

| Cationic Polymer | Dye Intermediate Structure | Color of Product |
| --- | --- | --- |
| polyethylenimine (m.w. 1200) | anthraquinone with Cl and NH$_2$ substituents | blue |
| polyethylenimine (m.w. 1200) | anthraquinone with OH and NH$_2$CH$_2$CH$_2$OH substituents | blue |
| polyethylenimine (m.w. 1200) | anthraquinone with OH and NH–C$_6$H$_4$–OCH$_3$ substituents | blue |

TABLE II-continued

| Cationic Polymer | Dye Intermediate Structure | Color of Product |
| --- | --- | --- |
| polyethylenimine (m.w. 1200) | 1-hydroxy-4-(4-hydroxyphenylamino)anthraquinone | blue |
| polyethylenimine (m.w. 1200) | 1-hydroxy-4-(4-aminophenylamino)anthraquinone | blue |
| polyethylenimine (m.w. 1200) | 1-hydroxy-4-(3-methoxyphenylamino)anthraquinone | blue |
| polyethylenimine (m.w. 1200) | 1-hydroxy-4-(4-diethylaminophenylamino)anthraquinone | blue |
| polyethylenimine (m.w. 1200) | 1,4-diamino-5-chloroanthraquinone | blue |
| polyethylenimine (m.w. 1200) | 1-chloroanthraquinone | red |
| polyethylenimine (m.w. 1200) | 1-chloro-2-methylanthraquinone | red |
| polyethylenimine (m.w. 200) | 1-chloro-2-nitro-4-aminobenzene | red |

TABLE II-continued

| Cationic Polymer | Dye Intermediate Structure | Color of Product |
|---|---|---|
| polyethylenimine (m.w. 1200) | (structure: triazine with two Cl, NH linked to dimethylphenyl-N=N-methoxy-nitrophenyl) | orange-red |
| polyethylenimine (m.w. 600) | (structure: dichlorotriazine-NHCH$_2$CH$_2$NH-anthraquinone) | red |
| polyethylenemine (m.w. 1200) | (structure: chloro-methoxy-dinitrobenzene) | golden-yellow |
| polyethylenimine (m.w. 1200) | (structure: chloro-nitroaniline) | orange-yellow |
| polyethylenimine (m.w. 1800) in which 25% of available amino groups have been stearoylated | (structure: chloroanthraquinone) | red |

Polymeric dyes based upon the cationic polymers described herein are as strongly substantive to natural fibers as are the polymers themselves. They dye instantly out of simple aqueous media and the color produced is inert to removal by strong acid, strong base, reducing agents, solvents, detergents or heat. However, substantivity is modestly decreased when the dyes are formulated with anionic polymers or anionic surfactants capable of forming anionic-cationic waxy complexes with the cationic polymeric dyes. These waxy materials produce colors that rub off or wash off to the extent that they may be employed in the formulation of temporary or semi-permanent dye products.

Color shade and intensity are influenced by the tinctorial power of the chromophore or chromophores attached to a given polymer backbone as well as by the concentration of the dye in the formulated dye bath. Individually, blue, yellow, and red polymeric dyes produce moderately instance colors, especially on bleached-waved hair. In admixture, either as an admixture of chromophores on a polymeric backbone or as a solution mixture of a plurality of polymeric dyes, color intensities in the black to brown range tend to be diminished. We have found that the preferred polymeric dyes for use in hair dyeing are those based upon polyethylenimine having a molecular weight range of 600 to 1800 and in which 0.1 to 10.0% of the available amino reaction sites are substituted with one or more chromophores. Useful cationic polymeric dyes based on cationic polymers with molecular weights from 300 to 200,000 have been prepared.

We have found that color intensity increases with increasing polymeric cationic dye concentration between 0.1 and 1.0%. Beyond 1.0% any further increase is marginal and there is generally little advantage in using concentrations beyond 5.0%. However, color intensity can be increased significantly at the 1-5% dye levels when certain polymers or surfactants are present in the formulated dye bath as discussed hereinafter.

It should also be noted that color intensity of these polymeric cationic dyes decreases as the self pH of the dye or formulated medium decreases. Dyes having a self pH of greater than 9 in water generally produce deeper colors than those having a self pH of less than 9. Color intensity produced at a pH of greater than 9 decreases significantly when the medium is acidified. Conversely, low color intensities produced by dyes having a self pH in the range, for example, of 6 to 7, increase significantly when the pH of the medium is adjusted to about 9.

Color intensity increases significantly between chromophore substitution levels of 1 to 5%. Between 5 and 10% chromophore substitution, further increases in color intensity are small with there generally being little advantage in going beyond 10%. This decrease in tinctorial power may be partly explained by the fact that as the level of substitution increases, the alkalinity of the polymer backbone decreases by removal of basic sites, thereby lowering the self pH of the resulting dye.

The color intensities of the dyes produced as described herein vary slightly as the cationic character of the polymer or solubility of the dye is altered or modified. We have found that acylation of the polymeric backbone decreases the cationic character of the polymer by converting the amine linkages to amides. This results in some decrease in color intensity, water solubility, and to some degree, substantivity especially if the dye is acylated within the range of 25 to 40% of available amino groups. Dyes based upon polymers having only secondary amines are less cationic, less soluble in water, less alkaline and less substantive than those based upon polyethylenimine. These dyes produce pale dyeings which do not intensify as much when the pH of the medium is changed and tend to be more easily removed from the hair. We have found that ethoxylation of dyes based upon the cationic polymeric backbones described herein increases their water solubility while changing color intensity only negligibly.

While the polymeric dyes of this invention cannot be removed with detergents or soaking dyed hair in strong acid, strong base, or organic solvents, the color produced on hair can be lightened considerably by hot dye stripping processes, such as, for example, a salt-solvent mixture containing 20% n-propanol, 16% sodium sulfate, 0.2% monoethanolamine and water, the composition having a pH of about 11. Another suitable dye stripping composition comprises a 15% sodium sulfoxylate formaldehyde solution in water containing 6% 2-naphthalenesulfonic acid, the composition having a pH of about 2.

A number of other types of additive materials can be employed to influence the color results obtained in the use of the dyes of this invention. Conventional carrier solvents such as benzyl alcohol, hexylene glycol, and benzyl urea may be employed to marginally increase depth of color. Levelling agents such as polymers, hydrophobic materials, salts, and swelling agents may also be employed to modify intensity and tone. In particular, anionic polymers such as sodium polystyrene sulfonate may be used to increase the intensity of dye-outs based upon chromophorically modified polyethylenimines.

Where it is desired to significantly decrease dye-out intensity, cationic, ampholytic, and fatty acid soap surfactants may be employed in the formulation. Nonionic and hydrotropic anionic surfactants, on the other hand, produce minimal changes and intensity and may be used to advantage as solubilizers where necessary. Conventional anionic detergents generally increase intensity significantly by virtue of producing a heavy dye coating on the hair. As the coating becomes more waxy, the substantivity of the color decreases because more rub-off occurs. This effect may be found useful in achieving semi-permanent dyeings with the dyes of this invention.

EXAMPLE VIII

The following hair dye composition was prepared.

| Ingredient | Percent by Weight |
| --- | --- |
| sodium cocomethyl tauride | 12.50 |
| lauricdiethanolamide | 7.00 |
| lauryl alcohol | 0.95 |
| hexylene glycol | 3.00 |
| reaction product of polyethylenimine (m.w. 1833) and 1-chloroanthraquinone (10% substitution) | 1.39 |
| water q.s. to 100.00 | pH 9.38 |

The dyeing properties of the above composition were evaluated by saturating a tress of bleached and waved human hair at a bath to hair ratio of 2:1 and allowing it to remain on the hair for approximately 15 minutes to simulate a color shampoo application. The hair was then water rinsed and air dried producing a pale red coloration.

EXAMPLE IX

A composition identical to that described in Example VIII was prepared except that the dye ingredient comprised 1.02% of the reaction product of polyethylenimine (m.w. 1800) and 1,4-diamino-5-nitroanthraquinone (substitution level 1.7%). Upon dye-out evaluation, the hair tress exhibited an attractive pale blue coloration.

EXAMPLE X

A composition identical to that described in Example VIII was prepared except that the dye ingredient comprised 1.11% of the reaction product of polyethylenimine (m.w. 1800) and 1-chloro-2,4-dinitrobenzene (substitution 1.0%) Upon dye-out evaluation, the hair tress exhibited an attractive pale yellow coloration.

EXAMPLE XI

The following hair dye composition was prepared.

| Ingredient | Percent by Weight |
| --- | --- |
| sodium cocomethyl tauride | 10.0 |
| lauricdiethanolamide | 5.0 |
| isopropanol | 10.0 |
| reaction product of polyethylenimine (m.w. 1800) and 1,4-diamino-5-nitroanthraquinone having a substitution level of 5% | 3.0 |
| water q.s. 100.00 | pH 10.05 |

The color result when evaluated by the method described in the above examples yields a medium pale blue color.

EXAMPLE XII

| Ingredient | Percent by Weight |
| --- | --- |
| reaction product of polyethylenimine (m.w. 1800) with 1,4-diamino-5-nitro-anthraquinone (1.7% substitution), 1-chloro-anthraquinone (4.5% substitution), and 1-chloro-2, 4-dinitrobenzene (2.5% substitution) | 5.0 |
| water | 15.0 |
| ethanol | 30.0 |
| aerosol propellant (50/50 mixture of propellant-11-propellant 12) | 50.0 |

The aerosol color spray composition was sprayed and combed through a tress of intact white human hair to produce a uniform grey-black coating. After the dye had been thoroughly distributed through the hair tress, it was rinsed with water and dried yielding an attractive silver-grey color.

We claim:

1. A method of dyeing human hair which comprises applying to said hair an effective amount of a composition comprising an aqueous medium containing up to 5.0% by weight of a cationic polymeric dye comprising the reaction product of a dye and a cationic polymer selected from the group consisting of polyethylenimine having a molecular weight of 300 to 200,000, polydiallylamine having a molecular weight of 10,000 to 2,000,000, and the reaction products obtained by the condensation of alkylene polyamines having 3 or more primary, secondary or tertiary amino groups separated by alkylene groups having 2 to 5 carbon atoms and having a molecular weight of 60 to 400 with difunctional compounds selected from the class consisting of dibasic acids having 2 to 54 carbon atoms, alpha-omega aliphatic dihalides having 2 to 10 carbon atoms, epihalohydrins and diepoxides having 4 to 18 carbon atoms, said reaction products having a molecular weight of 1,000 to 100,000, said polymer having condensed on a portion up to 25% of the primary and secondary amino groups thereof, a dye selected from the group consisting of azo, anthraquinone, nitro, nitroso, stilbene, diphenylmethane, triarylmethane, xanthene, acridene, quinoline, methine, thiazole, indamine, indophenol, azine, thiazine, lactone, aminoketone, hydroxyketone, indigoid and phthalocyanine.

2. A method of dyeing human hair as described in claim 1, in which up to 75% of the primary and secondary amino groups of said cationic polymer are reacted with alkylating or acylating agents having alkyl groups of 1 to 18 carbon atoms or with ethylene oxide.

3. A method of dyeing human hair as described in claim 1, in which the reacted amino groups are directly bonded to the dye molecule.

4. A method of dyeing human hair as described in claim 1, in which the reacted amino groups are bonded to the dye molecule through a reactive group introduced by reaction of said dye with a compound selected from the group consisting of vinyl sulfone, acylating agents, cyanuric halides, sulfonylating agents, and phosphorylating agents.

5. A method of dyeing human hair as described in claim 1, in which the polymer is condensed with two or more dyes.

6. A method of dyeing human hair as described in claim 1, in which said composition includes in addition a water soluble surfactant, said composition having a pH greater than 9.0.

7. A method of dyeing human hair as described in claim 1, in which the polymer is polyethylenimine having a molecular weight of 600 to 1800 and in which 0.1 to 10.0% of the amino groups are condensed with dye.

* * * * *